United States Patent
Krishnan (10) Patent No.: US 12,190,518 B1
(45) Date of Patent: Jan. 7, 2025

(54) SYSTEM AND METHOD FOR PNEUMONIA DETECTION USING IMAGE PROCESSING AND OBJECT DETECTION

(71) Applicant: Prithvi Sairaj Krishnan, Austin, TX (US)

(72) Inventor: Prithvi Sairaj Krishnan, Austin, TX (US)

( * ) Notice: Subject to any disclaimer, the term of this patent is extended or adjusted under 35 U.S.C. 154(b) by 0 days.

(21) Appl. No.: 18/757,788

(22) Filed: Jun. 28, 2024

(51) Int. Cl.
| | | |
|---|---|---|
| *G06K 9/00* | (2022.01) | |
| *G06T 7/00* | (2017.01) | |
| *G06V 10/776* | (2022.01) | |
| *G06V 10/82* | (2022.01) | |
| *G16H 10/60* | (2018.01) | |

(52) U.S. Cl.
CPC .......... *G06T 7/0014* (2013.01); *G06V 10/776* (2022.01); *G06V 10/82* (2022.01); *G16H 10/60* (2018.01); *G06T 2207/10116* (2013.01); *G06T 2207/20081* (2013.01); *G06T 2207/20084* (2013.01); *G06T 2207/30061* (2013.01); *G06V 2201/03* (2022.01)

(58) Field of Classification Search
CPC ......... G06T 7/0014; G06T 2207/10116; G06T 2207/20081; G06T 2207/20084; G06T 2207/30061; G06V 10/776; G06V 10/82; G06V 2201/03; G16H 10/60
See application file for complete search history.

(56) References Cited

U.S. PATENT DOCUMENTS

| | | |
|---|---|---|
| 2019/0006041 A1 | 1/2019 | Chiofolo |
| 2020/0093455 A1 | 3/2020 | Wang et al. |
| 2022/0366671 A1 | 11/2022 | López González et al. |
| 2023/0128966 A1* | 4/2023 | Tamal ............ G16H 30/40 |
| | | 382/128 |

(Continued)

FOREIGN PATENT DOCUMENTS

WO   WO-2021209887 A1 * 10/2021   .......... G06T 7/0012

OTHER PUBLICATIONS

Hammoudi, K., Benhabiles, H., Melkemi, M. et al. Deep Learning on Chest X-ray Images to Detect and Evaluate Pneumonia Cases at the Era of COVID-19. J Med Syst 45, 75 (2021). https://doi.org/10.1007/s10916-021-01745-4 https://link.springer.com/article/10.1007/s10916-021-01745-4.

(Continued)

*Primary Examiner* — Xin Jia
(74) *Attorney, Agent, or Firm* — Carson Patents; Gregory D Carson (57) ABSTRACT

The system and method for pneumonia detection using image processing and object detection in chest X-ray images utilizes an ensemble of deep learning models, including GoogLeNet, ResNet-18, and DenseNet-121. The process begins with the acquisition and pre-processing of medical images to standardize and partition them into training, validation, and testing subsets. The convolutional neural networks (CNNs) are trained and fine-tuned on the training subset, and their performance is evaluated using the validation subset with metrics such as accuracy, precision, recall, (Continued)

and F1-score. The system computes an ensembled probability score to make the final prediction, ensuring high accuracy. This method also integrates clinical data for improved diagnostic precision.

12 Claims, 3 Drawing Sheets

(56) References Cited

U.S. PATENT DOCUMENTS

2023/0230680 A1* 7/2023 Ward .................. G06T 11/20
382/128

OTHER PUBLICATIONS

Hashmi MF, Katiyar S, Keskar AG, Bokde ND, Geem ZW. Efficient Pneumonia Detection in Chest Xray Images Using Deep Transfer Learning. Diagnostics. 2020; 10(6):417. https://doi.org/10.3390/diagnostics10060417 https://www.mdpi.com/2075-4418/10/6/417.

Rachna Jain, Preeti Nagrath, Gaurav Kataria, V. Sirish Kaushik, D. Jude Hemanth, Pneumonia detection in chest X-ray images using convolutional neural networks and transfer learning, Measurement, vol. 165, 2020, 108046, ISSN 0263-2241, https://doi.org/10.1016/j.measurement.2020.108046 https://www.sciencedirect.com/science/article/pii/S0263224120305844.

Rahman T, Chowdhury MEH, Khandakar A, Islam KR, Islam KF, Mahbub ZB, Kadir MA, Kashem S. Transfer Learning with Deep Convolutional Neural Network (CNN) for Pneumonia Detection Using Chest X-ray. Applied Sciences. 2020; 10(9):3233. https://doi.org/10.3390/app10093233 https://www.mdpi.com/2076-3417/10/9/3233.

* cited by examiner

SYSTEM AND METHOD FOR PNEUMONIA DETECTION USING IMAGE PROCESSING AND OBJECT DETECTION

STATEMENT REGARDING PRIOR DISCLOSURES BY THE INVENTOR OR JOINT INVENTOR

The inventor/application disclosed the invention on or about Feb. 21, 2024 to a high school science fair at The Greater Austin Regional Science and Engineering Fair in Austin, Texas.

The inventor/application disclosed the invention on or about Jun. 1, 2024 to a peer reviewed journal titled The Journal of Student Research is the Journal. Additionally, Applicant has applied for The International Symposium on Networks, Computers, and Communications which is in Washington, D.C. October 2024.

BACKGROUND OF THE INVENTION

Technical Field

This invention relates generally to a system for pneumonia detection using image processing and object detection software in images. This invention relates more particularly to an apparatus/device to implement a system for pneumonia detection.

This invention relates generally to a method for pneumonia detection using image processing and object detection software in images. This invention relates more particularly to an apparatus/device to implement a method for pneumonia detection.

Background Art

Today, there are various systems and methods for detecting lung infections, particularly focusing on COVID-19 and pneumonia, through chest X-ray images using advanced image processing and deep learning techniques. One system uses median filtering and machine learning techniques like Random Forest and CNNs, deployed via FLASK Python for user interaction. Another method leverages DenseNet CNNs for remote SARS-COV-2 classification, aiming to alleviate healthcare workloads. A different system processes X-rays through multiple CNNs to detect anomalies, aiding radiologists by automating preliminary diagnoses. Other systems describe using CNNs for medical image analysis, focusing on pneumonia detection, and integrating data processing, model training, and evaluation to enhance diagnostic precision.

Specifically, one prior art outlines a system and method for detecting lung infections through X-ray images, specifically targeting COVID-19, normal lung conditions, lung opacity, and viral pneumonia. It describes the use of various image processing techniques, including the median filter to remove noise and visualization with the matplotlib package. Machine learning techniques such as Random Forest classifier and deep learning techniques like CNN and DCNN are applied to optimize time parameters. The system is deployed using FLASK Python, enabling users to upload X-ray images and get detection results.

Another prior art presents a method for classifying the presence of SARS-COV-2 via chest radiographs using deep learning. The system uses a DenseNet-based convolutional neural network trained on frontal chest X-rays to classify images into categories of COVID-19, pneumonia, and normal. The method aims to provide quick remote diagnosis, reducing the workload on healthcare professionals and helping manage patient queues in hospitals. The system leverages transfer learning and data augmentation to improve accuracy with limited datasets.

Additionally, there is a prior art that describes a method and system for identifying anomalies in X-ray images using neural networks. The system processes chest X-rays through multiple convolutional neural networks, each trained to detect specific graphic patterns associated with various pathologies. These probabilities are then fed into a fully connected neural network to determine the presence of anomalies. The invention aims to aid radiologists by automating the preliminary identification of abnormalities, helping prioritize diagnostic worklists.

Another prior art outlines a system and method for medical image analysis using artificial intelligence. It details how convolutional neural networks (CNNs) can be used to process medical images, such as X-rays, to detect abnormalities. The system includes modules for image acquisition, preprocessing, training, and evaluation, and aims to provide accurate and efficient diagnostic tools to assist healthcare professionals.

Also available in the prior art is a method and system for detecting pneumonia using chest X-ray images processed by deep learning models. The system employs convolutional neural networks (CNNs) and various image processing techniques to analyze medical images and identify signs of pneumonia. The method includes data acquisition, preprocessing, model training, and evaluation to ensure high diagnostic accuracy.

Another prior art describes a method for medical diagnosis using deep learning on chest X-ray images. It emphasizes the use of a multi-layer convolutional neural network architecture to classify medical images and detect conditions like pneumonia and other lung diseases. The system integrates data processing, model training, and evaluation to improve diagnostic precision and assist healthcare providers in early detection and treatment planning.

Additionally, there is a prior art that presents a system for detecting lung infections, particularly focusing on COVID-19, using chest X-ray images and machine learning techniques. The system utilizes image processing methods and deep learning models to analyze X-rays and identify infections. It includes a detailed description of the system's architecture, data processing, and deployment for practical use in clinical settings.

Lastly, there is a prior art that details a method for the classification and detection of lung diseases using artificial intelligence on medical images. The system processes X-ray images through various convolutional neural network models to detect and classify different types of lung infections, including pneumonia and COVID-19. The document outlines the technical specifications, model training, and evaluation processes to ensure accurate diagnosis and support healthcare professionals.

In light of the foregoing prior art, there is a need for a system that provides early and accurate pneumonia diagnosis from chest X-rays, reduces radiologists' workload, operates in low-resource settings, ensures objective analysis with high sensitivity, and integrates into clinical decision support systems with a flexible, adaptable design.

BRIEF SUMMARY OF THE INVENTION

The system for pneumonia detection using image processing and object detection includes several modules: a data acquisition module for obtaining medical image datasets, a pre-processing module for standardizing and partitioning the dataset, and a model training module that uses convolutional neural networks (CNNs) to optimize pneumonia detection. The system also includes a model evaluation module to assess performance using various metrics, and a simulation module for executing computations on a cloud-based platform. Additionally, the system can utilize an ensemble of deep learning models, such as GoogLeNet, ResNet-18, and DenseNet-121, to achieve high accuracy in pneumonia detection and integrates clinical data to enhance diagnostic precision. The method for using this system involves acquiring, pre-processing, training, tuning, and evaluating the dataset, and executing the necessary computations on a cloud-based platform.

According to a first aspect of the invention, there is a system for detecting pneumonia in chest X-ray images comprising: a data acquisition module configured to obtain a dataset of medical images having a set of pneumonia-infected lung images and a set of healthy lung images; a pre-processing module configured to standardize and partition said dataset of medical images into a training subset, a validation subset, and a testing subset; a model training module comprising at least one convolutional neural network (CNN) configured for image processing and object detection wherein said model training module is configured to fine-tune said CNN using said training subset to optimize performance of said CNN for a pneumonia detection; a model evaluation module configured to evaluate said training module using said validation subset and then compute a set of performance metrics; and a simulation module configured to execute a computation and a simulation on a cloud-based platform wherein said system is configured to detect a pneumonia condition from said chest X-ray image submitted to said system for an evaluation.

According to a second aspect of the invention, there is a system for detecting pneumonia in chest X-ray images wherein said model training module utilizes an ensemble combination of at least three deep learning models configured in a serial operation to achieve an accuracy detection rate of not less than ninety-eight percent accuracy in said pneumonia detection.

According to a third aspect of the invention, there is a system for detecting pneumonia in chest X-ray images wherein said model evaluation module computes said set of performance metrics comprising an accuracy determined from percentage of a set of pneumonia predictions correct, a precision determined from said set of pneumonia predictions of when said system detects a pneumonia by calculating the ratio of true positive predictions to all positive predictions, a recall determined from an ability of said system to determine all actual pneumonia cases by computing the ratio of true positive predictions to the total real pneumonia cases, and an F1-score determined from said precision and said recall, configured to provide an early and an accurate pneumonia screening thus enabling a life-saving treatment.

According to a fourth aspect of the invention, there is a system for detecting pneumonia in chest X-ray images wherein said simulation module utilizes said cloud-based platform such as a Python environment having libraries for implementing an image processing algorithm and an object detection algorithm.

According to a fifth aspect of the invention, there is a system for detecting pneumonia in chest X-ray images further comprising a multi-modal module configured to integrate said chest X-ray images with a clinical data, including at least a laboratory data and a patient history, thus improving a diagnostic precision and a reliability.

According to a sixth aspect of the invention, there is a method for detecting pneumonia in a chest X-ray image comprising: acquiring a dataset of medical images comprising at least three pneumonia-infected lung images and at least three healthy lung images; pre-processing said dataset of medical images to standardize and partition said dataset of medical images into a training subset, a validation subset, and a testing subset; training one or more convolutional neural networks (CNN) for an image processing and an object detection using said training subset; tuning said training to optimize performance for a pneumonia detection; evaluating said training using said validation subset and computing a set of performance metrics; executing computations and simulations on a cloud-based platform; and detecting a pneumonia in said chest X-ray image based on said training subset and said validation subset.

According to a seventh aspect of the invention, there is a method for detecting pneumonia in a chest X-ray image wherein training said CNN comprises utilizing an ensemble combination of multiple deep learning models configured in a serial operation to achieve an accuracy detection rate of not less than ninety-eight percent in said pneumonia detection.

According to an eighth aspect of the invention, there is a method for detecting pneumonia in a chest X-ray image wherein computing said set of performance metrics comprises: an accuracy determined from percentage of a set of pneumonia predictions correct, a precision determined from said set of pneumonia predictions by calculating the ratio of true positive predictions to all positive predictions, a recall determined from an ability to determine all actual pneumonia cases by computing the ratio of true positive predictions to the total real pneumonia cases, and an F1-score determined from said precision and said recall, configured to provide an early, and an accurate pneumonia screening thus enabling a life-saving treatment.

According to a ninth aspect of the invention, there is a method for detecting pneumonia in a chest X-ray image wherein executing necessary computations and simulations comprises utilizing said cloud-based platform having a web based internet environment comprising libraries for implementing an image processing algorithm and an object detection algorithm.

According to a tenth aspect of the invention, there is a method for detecting pneumonia in a chest X-ray image further configured to integrate said chest X-ray image with a clinical data, including at least a laboratory data and a patient history, thus improving a diagnostic precision and a reliability.

Advantages of the system and methods of the present invention include the following:

Early and Accurate Diagnosis: The system can accurately detect pneumonia from chest X-rays, enabling early diagnosis, which is crucial for effective treatment and management.

Reduces Burden on Radiologists: By flagging likely pneumonia cases, the automated system assists radiologists, reducing their workload and time spent examining large volumes of X-rays manually. This also ensures more consistent diagnoses.

Applicable in Low-Resource Settings: Requiring only digitized chest X-ray images, the system can be used in areas with limited access to specialists, allowing timely diagnosis in underserved communities.

Objective Analysis: The system uses deep learning models to make classifications in an automated, unbiased manner, ensuring consistency compared to human-dependent analyses.

High Sensitivity: The system has achieved high sensitivity/recall, making it effective at detecting actual pneumonia cases and reducing false negatives.

Integration into Clinical Decision Support: The system can potentially be integrated into hospital picture archiving and communication systems or electronic medical records, serving as a clinical decision support tool to improve patient management.

Domain-Independent Design: The ensemble deep learning framework is flexible and can be adapted by training the model on different chest X-ray images and disease recognition patterns.

The invention will now be described, by way of example only, with reference to the accompanying drawings in which:

DETAILED DESCRIPTION OF THE INVENTION

The detailed embodiments of the present invention are disclosed herein. The disclosed embodiments are merely exemplary of the invention, which may be embodied in various forms. The details disclosed herein are not to be interpreted as limiting, but merely as the basis for the claims and as a basis for teaching one skilled in the art how to make and use the invention.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Throughout this specification, the word "comprise," or variations thereof such as "comprises" or "comprising," will be understood to imply the inclusion of a stated element, integer or step, or group of elements integers or steps, but not the exclusion of any other element, integer or step, or group of elements, integers or steps.

Index of Labelled Features in Figures. Features are listed in numeric order by FIGURE in numeric order.

Figure 1:
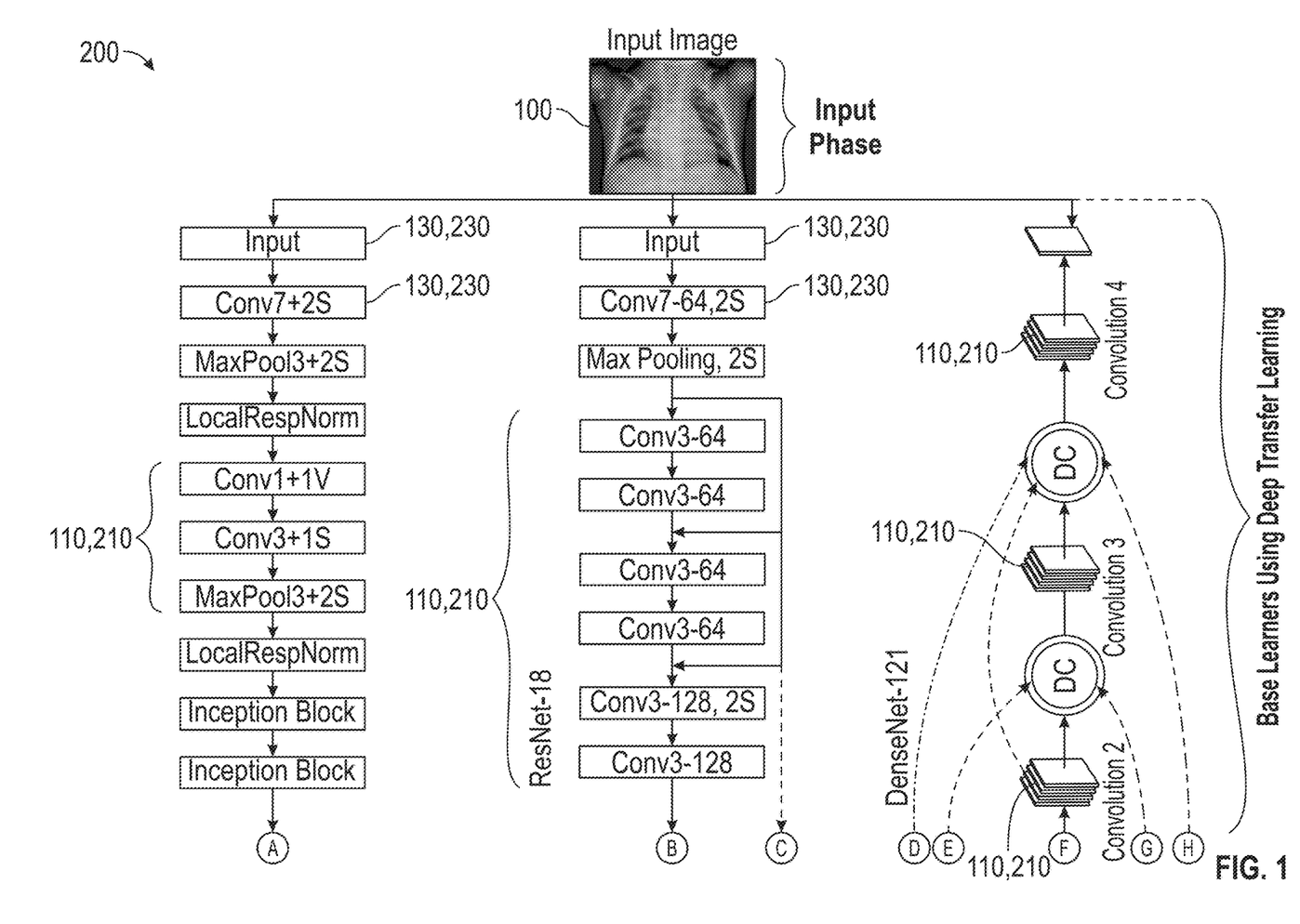
FIG. 1 is a flowchart of the process which involves inputting a chest X-ray image, generating evaluation metrics from multiple models to compute weights, calculating an ensembled probability score, and making a final prediction of pneumonia or normal lungs, ensuring high accuracy and integrating clinical data for enhanced diagnostic precision of the system and method for pneumonia detection using image processing and object detection according to the invention.

Referring to the Figures, there is shown in FIG. 1 the following features:

Element 100 which is a data acquisition module configured to obtain a dataset of medical images having a set of pneumonia-infected lung images and a set of healthy lung images.

Element 110 which is a pre-processing module configured to standardize and partition said dataset of medical images into a training subset, a validation subset, and a testing subset.

Element 120 which is a model training module comprising at least one convolutional neural network (CNN) configured for image processing and object detection wherein said model training module is configured to fine-tune said CNN using said training subset to optimize performance of said CNN for pneumonia detection.

Element 130 which is a model evaluation module configured to evaluate said training module using said validation subset and then compute a set of performance metrics.

Element 140 which is a simulation module configured to execute a computation and a simulation on a cloud-based platform.

The system of element 100 wherein said model training module utilizes an ensemble combination of at least three deep learning models, such as GoogLeNet, ResNet-18, and DenseNet-121, configured in a serial operation to achieve an accuracy detection rate of not less than 98% in said pneumonia detection.

The system of element 100 wherein said model evaluation module computes said set of performance metrics comprising:

Element 150 which is an accuracy determined from percentage of a set of pneumonia predictions correct.

Element 160 which is a precision determined from said set of pneumonia predictions by calculating the ratio of true positive (correct pneumonia) predictions to all positive predictions.

Element 170 which is a recall (sensitivity) determined from an ability of said system to determine all actual pneumonia cases by computing the ratio of true positive predictions to the total real pneumonia cases.

Element 180 which is an F1-score determined from said precision and said recall configured to provide an early and accurate pneumonia screening thus enabling a life-saving treatment.

The system of element 100 wherein said simulation module utilizes said cloud-based platform such as a Python environment having libraries for implementing an image processing algorithm and an object detection algorithm.

The system of element 100 further comprising a multi-modal module configured to integrate said chest X-ray images with clinical data, including at least laboratory data and patient history, thus improving diagnostic precision and reliability.

A method for detecting pneumonia in a chest X-ray image comprising:

Element 200 which is acquiring a dataset of medical images comprising at least three pneumonia-infected lung images and at least three healthy lung images.

Element 210 which is pre-processing said dataset of medical images to standardize and partition said dataset of medical images into a training subset, a validation subset, and a testing subset.

Element 220 which is training one or more convolutional neural networks (CNN) for image processing and object detection using said training subset.

Element 230 which is tuning said training to optimize performance for pneumonia detection.

Element 240 which is evaluating said training using said validation subset and computing a set of performance metrics.

Element 250 which is executing computations and simulations on a cloud-based platform.

Element 260 which is detecting pneumonia in said chest X-ray image based on said training subset and said validation subset.

The method of element 200 wherein training said CNN comprises utilizing an ensemble combination of multiple deep learning models such as GoogLeNet, ResNet-18, and DenseNet-121, configured in a serial operation to achieve an accuracy detection rate of not less than 98% in said pneumonia detection.

The method of element 200 wherein computing said set of performance metrics comprises:

Element 270 which is an accuracy determined from percentage of a set of pneumonia predictions correct.

Element 280 which is a precision determined from said set of pneumonia predictions by calculating the ratio of true positive (correct pneumonia) predictions to all positive predictions.

Element 290 which is a recall (sensitivity) determined from an ability to determine all actual pneumonia cases by computing the ratio of true positive predictions to the total real pneumonia cases.

Element 300 which is an F1-score determined from said precision and said recall configured to provide an early and accurate pneumonia screening thus enabling a life-saving treatment.

The method of element 200 wherein executing necessary computations and simulations comprises utilizing said cloud-based platform having a web-based internet environment such as Python comprising libraries for implementing an image processing algorithm and an object detection algorithm.

The method of element 200 further configured to integrate said chest X-ray image with clinical data, including at least laboratory data and patient history, thus improving diagnostic precision and reliability.

To create a system for detecting pneumonia in chest X-ray images, several components and processes are involved, each with specific purposes and functions. The system begins with the data acquisition module, whose primary purpose is to obtain a dataset of medical images. This module is configured to collect and store medical images, including a set of pneumonia-infected lung images and a set of healthy lung images, ensuring a comprehensive dataset for the system.

The next component is the pre-processing module, which serves to standardize and partition the dataset. Standardization ensures that all images have a uniform format, size, and quality, facilitating consistent processing. The module then partitions the standardized dataset into three subsets: a training subset used to train the model, a validation subset used to validate and tune the model during training, and a testing subset used to evaluate the final model's performance.

Following pre-processing, the model training module comes into play, designed to train a model to detect pneumonia in images. This module utilizes a Convolutional Neural Network (CNN), a type of deep learning model specifically tailored for image processing and object detection. The training subset is used to fine-tune the CNN, adjusting the model parameters to optimize its performance in detecting pneumonia.

Once the model is trained, the model evaluation module assesses its effectiveness. This module uses the validation subset to evaluate the model's performance and make necessary adjustments. Performance metrics, such as accuracy, precision, recall, and F1 score, are computed to quantify the model's effectiveness, ensuring it meets the desired standards of accuracy and reliability.

The simulation module is then employed to execute computations and simulations. This module performs intensive computations on a cloud-based platform, such as a Python environment equipped with libraries for implementing image processing and object detection algorithms. This setup ensures robust performance and scalability, crucial for handling large datasets and complex computations.

To enhance diagnostic precision and reliability, the multi-modal module integrates medical images with clinical data. This module combines chest X-ray images with clinical data, including laboratory data and patient history. The integration of these data sources provides a more comprehensive view of the patient's condition, thereby enhancing the diagnostic accuracy and reliability of the system.

The detailed workflow of this system involves several steps: collecting and storing a comprehensive dataset of chest X-ray images, standardizing and partitioning the images, training a CNN for pneumonia detection, evaluating the model's performance using validation metrics, executing further computations on a cloud-based platform, and integrating chest X-ray images with clinical data. This structured approach leverages advanced machine learning techniques, cloud computing, and multi-modal data integration to develop a reliable and comprehensive pneumonia detection tool, ensuring efficient and effective diagnostic outcomes.

To create a software application for detecting pneumonia in chest X-ray images, the process involves several detailed steps. The initial step is to acquire a dataset of medical images. This step's objective is to collect a dataset that includes both pneumonia-infected lung images and healthy lung images. The requirements are to have at least three pneumonia-infected lung images and at least three healthy lung images. The procedure involves sourcing images from medical databases, hospitals, or publicly available datasets and ensuring the images are correctly labeled to distinguish between pneumonia-infected and healthy lungs.

Next, the dataset must be pre-processed to ensure consistency and prepare it for model training. Standardization involves resizing images to a uniform dimension and normalizing pixel values to a common scale. The dataset is then partitioned into three subsets: a training subset for training the CNN, a validation subset for tuning and validating the model, and a testing subset for evaluating the final performance of the model.

The third step is to train Convolutional Neural Networks (CNNs) to develop a model capable of detecting pneumonia from chest X-ray images. This involves using the training subset to train one or more CNNs designed for image processing and object detection. The implementation requires a suitable architecture, such as VGG16, ResNet, or a custom CNN, and configuring training parameters like learning rate, batch size, and number of epochs.

Following training, the next step is to tune the training to optimize the model's performance specifically for pneumonia detection. This involves adjusting hyperparameters based on performance on the validation subset and implementing techniques such as learning rate scheduling, dropout, and data augmentation. Performance metrics like accuracy, precision, recall, and F1 score should be monitored throughout this process.

Once the model is trained and tuned, it needs to be evaluated to assess its performance using the validation subset. This involves using the validation subset to evaluate the model and making further adjustments if necessary. A set of performance metrics, including accuracy, precision, recall, and F1 score, is computed to gauge the model's effectiveness.

The sixth step involves executing computations and simulations efficiently. This can be done using a cloud-based platform, such as AWS, Google Cloud, or Azure, to handle the computational load. The image processing and object detection algorithms should be implemented using appropriate libraries in a Python environment, such as TensorFlow, Keras, or PyTorch.

The next objective is to apply the trained and validated model to new chest X-ray images to detect pneumonia. This involves inputting the new chest X-ray image into the trained CNN model, using the model to predict whether the image shows pneumonia or a healthy lung, and outputting the prediction results.

The final step is to enhance diagnostic precision and reliability by integrating clinical data with image data. This involves combining chest X-ray images with clinical data, including laboratory results and patient history, to provide a more comprehensive analysis of the patient's condition and improve diagnostic accuracy.

For software implementation, Python is the recommended programming language, with TensorFlow or PyTorch for deep learning, OpenCV or PIL for image processing, and Scikit-learn for performance metrics. The software implementation involves several scripts: a data acquisition script to acquire and label the dataset, a pre-processing script to standardize and partition the dataset, a training script to define and train the CNN model, a tuning script to implement hyperparameter tuning and optimization techniques, an evaluation script to evaluate the model and compute performance metrics, a deployment script to deploy the model on a cloud platform and handle predictions, and an integration script to combine clinical data with image data for improved diagnostic accuracy.

This method ensures a comprehensive approach to developing a software application for pneumonia detection using chest X-ray images, leveraging machine learning, cloud computing, and multi-modal data integration for efficient, effective, and comprehensive diagnostic outcomes, thus enabling early and accurate pneumonia screening and life-saving treatment.

Accuracy, precision, recall, and F1-score are four crucial metrics used to comprehensively assess and measure the success of the machine learning model employed in this pneumonia detection invention. Achieving high performance across these metrics is essential for an effective and clinically valuable system.

Accuracy quantifies how often the model correctly predicts both pneumonia cases and healthy cases out of all chest X-ray images evaluated. The invention claims an accuracy of over 98%, indicating an exceptional overall correct prediction rate.

Precision evaluates how accurate the model's predictions are when it detects pneumonia by calculating the ratio of true positive (correct pneumonia) predictions to all positive predictions. High precision ensures minimal false positive errors, which could lead to unnecessary treatment.

Recall (Sensitivity) measures the model's ability to catch all actual pneumonia cases by computing the ratio of true positive predictions to the total real pneumonia cases. High recall prevents missing pneumonia cases that require timely treatment.

The F1-score balances precision and recall into one metric, optimizing the trade-off to maximize both correct pneumonia detection and minimize missed and incorrect cases.

For this invention to provide early, accurate pneumonia screening and enable life-saving treatment, it is critical to achieve: high accuracy overall, high precision to confidently treat detected cases, high recall to not miss cases requiring urgent care, and high F1 establishing reliable performance By claiming over 98% accuracy along with high precision, recall, and F1-score, this invention demonstrates its capability as a robust and clinically valuable automated piece of research for early pneumonia detection from chest X-rays, meeting the key performance requirements.

In a preferred embodiment of the invention, there is a system for detecting pneumonia in chest X-ray images comprising: a data acquisition module configured to obtain a dataset of medical images having a set of pneumonia-infected lung images and a set of healthy lung images; a pre-processing module configured to standardize and partition said dataset of medical images into a training subset, a validation subset, and a testing subset; a model training module comprising at least one convolutional neural network (CNN) configured for image processing and object detection wherein said model training module is configured to fine-tune said CNN using said training subset to optimize performance of said CNN for a pneumonia detection; a model evaluation module configured to evaluate said training module using said validation subset and then compute a set of performance metrics; and a simulation module configured to execute a computation and a simulation on a cloud-based platform wherein said system is configured to detect a pneumonia condition from said chest X-ray image submitted to said system for an evaluation.

In an alternate embodiment of the invention, there is a system for detecting pneumonia in chest X-ray images wherein said model training module utilizes an ensemble combination of at least three deep learning models (such as GoogLeNet, ResNet-18, and/or DenseNet-121) configured in a serial operation to achieve an accuracy detection rate of not less than ninety-eight percent accuracy in said pneumonia detection.

In an alternate embodiment of the invention, there is a system for detecting pneumonia in chest X-ray images wherein said model evaluation module computes said set of performance metrics comprising an accuracy determined from percentage of a set of pneumonia predictions correct, a precision determined from said set of pneumonia predictions of when said system detects a pneumonia by calculating the ratio of true positive (correct pneumonia) predictions to all positive predictions, a recall (sensitivity) determined from an ability of said system to determine all actual pneumonia cases by computing the ratio of true positive predictions to the total real pneumonia cases, and an F1-score determined from said precision and said recall, configured to provide an early and an accurate pneumonia screening thus enabling a life-saving treatment.

In an alternate embodiment of the invention, there is a system for detecting pneumonia in chest X-ray images wherein said simulation module utilizes said cloud-based platform (such as a Python environment) having libraries for implementing an image processing algorithm and an object detection algorithm.

In an alternate embodiment of the invention, there is a system for detecting pneumonia in chest X-ray images further comprising a multi-modal module configured to integrate said chest X-ray images with a clinical data, including at least a laboratory data and a patient history, thus improving a diagnostic precision and a reliability.

In a preferred embodiment of the invention, there is a method for detecting pneumonia in a chest X-ray image comprising: acquiring a dataset of medical images comprising at least three pneumonia-infected lung images and at least three healthy lung images; pre-processing said dataset of medical images to standardize and partition said dataset of medical images into a training subset, a validation subset, and a testing subset; training one or more convolutional neural networks (CNN) for an image processing and an object detection using said training subset; tuning said training to optimize performance for a pneumonia detection; evaluating said training using said validation subset and computing a set of performance metrics; executing computations and simulations on a cloud-based platform; and detecting a pneumonia in said chest X-ray image based on said training subset and said validation subset.

In an alternate embodiment of the invention, there is a method for detecting pneumonia in a chest X-ray image wherein training said CNN comprises utilizing an ensemble combination of multiple deep learning models (such as GoogLeNet, ResNet-18, and DenseNet-121) configured in a serial operation to achieve an accuracy detection rate of not less than ninety-eight percent in said pneumonia detection.

In an alternate embodiment of the invention, there is a method for detecting pneumonia in a chest X-ray image wherein computing said set of performance metrics comprises: an accuracy determined from percentage of a set of pneumonia predictions correct, a precision determined from said set of pneumonia predictions by calculating the ratio of true positive (correct pneumonia) predictions to all positive predictions, a recall (sensitivity) determined from an ability to determine all actual pneumonia cases by computing the ratio of true positive predictions to the total real pneumonia cases, and an F1-score determined from said precision and said recall, configured to provide an early, and an accurate pneumonia screening thus enabling a life-saving treatment.

In an alternate embodiment of the invention, there is a method for detecting pneumonia in a chest X-ray image wherein executing necessary computations and simulations comprises utilizing said cloud-based platform having a web based internet environment (such as Python) comprising libraries for implementing an image processing algorithm and an object detection algorithm.

In an alternate embodiment of the invention, there is a method for detecting pneumonia in a chest X-ray image further configured to integrate said chest X-ray image with a clinical data, including at least a laboratory data and a patient history, thus improving a diagnostic precision and a reliability.

The advantages of the present invention include:

Early and Accurate Diagnosis: The new system leverages advanced deep learning algorithms to analyze chest X-rays and accurately detect signs of pneumonia. This early and precise detection is critical because it allows for prompt treatment, which can significantly improve patient outcomes. Early diagnosis helps in initiating the right medical interventions before the disease progresses, potentially reducing complications and improving recovery rates.

Reduces Burden on Radiologists: Radiologists are often overwhelmed by the sheer volume of X-rays they need to review daily. The automated system can assist by pre-screening X-rays and highlighting those that likely show signs of pneumonia. This not only speeds up the diagnostic process but also reduces the workload on radiologists, allowing them to focus on more complex cases. Additionally, the system provides consistent results, minimizing the variability that can occur with human analysis.

Applicable in Low-Resource Settings: In many parts of the world, access to specialized medical professionals is limited. The system only requires digitized chest X-ray images, making it feasible to deploy in remote or underserved areas. This accessibility means that even in low-resource settings, healthcare providers can diagnose pneumonia accurately and promptly, leading to better patient outcomes in regions where medical resources are scarce.

Objective Analysis: Human analysis of medical images can be subjective, with different radiologists potentially interpreting the same X-ray in various ways. The automated system, however, uses deep learning models to analyze images in a standardized and unbiased manner. This objectivity ensures consistent and reliable diagnoses, reducing the risk of human error and variability in interpreting the results.

High Sensitivity: The system has been evaluated and found to have high sensitivity, meaning it is particularly good at identifying actual cases of pneumonia. High sensitivity is crucial because it reduces the number of false negatives-cases where pneumonia is present but not detected. By minimizing false negatives, the system ensures that more patients receive the necessary treatment promptly.

Integration into Clinical Decision Support: The system can be integrated into existing hospital infrastructures such as picture archiving and communication systems (PACS) or electronic medical records (EMRs). This integration allows the automated pneumonia detection tool to function as a part of clinical decision support systems, aiding healthcare professionals in making more informed decisions and improving overall patient management.

Domain-Independent Design: The system is designed using an ensemble deep learning framework, which is highly adaptable. This means it can be trained on different sets of chest X-ray images and various disease recognition patterns, making it versatile and applicable to a wide range of medical imaging scenarios. This flexibility ensures that the system can be customized and optimized for different clinical environments and diagnostic needs.

Additionally the present invention can identify other diseases after long training.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

Although the invention has been explained in relation to various embodiments, it is to be understood that many other possible modifications and variations can be made without departing from the spirit and scope of the invention.

The invention claimed is:

1. A system for detecting pneumonia in chest X-ray images comprising:
a data acquisition module configured to obtain a dataset of medical images having a set of pneumonia-infected lung images and a set of healthy lung images;

a pre-processing module configured to standardize and partition said dataset of medical images into a training subset, a validation subset, and a testing subset;

a model training module comprising at least one convolutional neural network (CNN) configured for image processing and object detection, wherein said model training module is configured to fine-tune said CNN using said training subset to optimize performance of said CNN for pneumonia detection;

a model evaluation module configured to evaluate said model training module using said validation subset and then compute a set of performance metrics; and a simulation module configured to execute a computation and a simulation on a cloud-based platform;

wherein said system is configured to detect a pneumonia condition from said chest X-ray image and said model training module utilizes an ensemble combination of at least two deep learning models; and wherein said model training module utilizes an ensemble combination of at least two deep learning models configured in a serial operation to achieve a detection rate of not less than ninety-eight percent accuracy in said pneumonia detection.

2. The system of claim 1 wherein said simulation module utilizes said cloud-based platform such as a Python environment having libraries for implementing an image processing algorithm and an object detection algorithm.

3. The system of claim 1 further comprising a multimodal module configured to integrate said chest X-ray images with a clinical data, including at least a laboratory data and a patient history, thus improving a diagnostic precision and a reliability.

4. The system of claim 1 wherein said simulation module utilizes said cloud-based platform such as a Python environment having libraries for implementing an image processing algorithm and an object detection algorithm.

5. The system of claim 1 further comprising a multimodal module configured to integrate said chest X-ray images with a clinical data, including at least a laboratory data and a patient history, thus improving a diagnostic precision and a reliability.

6. A system for detecting pneumonia in chest X-ray images comprising:

a data acquisition module configured to obtain a dataset of medical images having a set of pneumonia-infected lung images and a set of healthy lung images;

a pre-processing module configured to standardize and partition said dataset of medical images into a training subset, a validation subset, and a testing subset;

a model training module comprising at least one convolutional neural network (CNN) configured for image processing and object detection, wherein said model training module is configured to fine-tune said CNN using said training subset to optimize performance of said CNN for pneumonia detection;

a model evaluation module configured to evaluate said model training module using said validation subset and then compute a set of performance metrics; and a simulation module configured to execute a computation and a simulation on a cloud-based platform;

wherein said system is configured to detect a pneumonia condition from said chest X-ray image and said model training module utilizes an ensemble combination of at least two deep learning models;

wherein said model evaluation module computes said set of performance metrics comprising:

an accuracy determined from the percentage of a set of pneumonia predictions correct;

a precision determined from said set of pneumonia predictions by calculating the ratio of true positive pneumonia predictions to all positive pneumonia predictions;

a recall determined from an ability of said system to detect all actual pneumonia cases by computing the ratio of true positive pneumonia predictions to the total real pneumonia cases; and an F1-score determined from said precision and said recall;

wherein said system is configured to provide early and accurate pneumonia screening, thus enabling life-saving treatment.

7. A method for detecting pneumonia in a chest X-ray image comprising:

acquiring a dataset of medical images comprising at least three pneumonia-infected lung images and at least three healthy lung images;

pre-processing said dataset of medical images to standardize and partition said dataset of medical images into a training subset, a validation subset, and a testing subset;

training one or more convolutional neural networks (CNN) for an image processing and an object detection using said training subset;

tuning said training to optimize performance for a pneumonia detection;

evaluating said training using said validation subset and computing a set of performance metrics;

executing computations and simulations on a cloud-based platform; and detecting a pneumonia in said chest X-ray image based on said training subset and said validation subset;

wherein training said CNN comprises utilizing an ensemble combination of multiple deep learning models configured in a serial operation to achieve an accuracy detection rate of not less than ninety-eight percent in said pneumonia detection.

8. The method of claim 7 wherein executing necessary computations and simulations comprises utilizing said cloud-based platform having a web based internet environment comprising libraries for implementing an image processing algorithm and an object detection algorithm.

9. The method of claim 7 further configured to integrate said chest X-ray image with a clinical data, including at least a laboratory data and a patient history, thus improving a diagnostic precision and a reliability.

10. The method of claim 7 wherein executing necessary computations and simulations comprises utilizing said cloud-based platform having a web based internet environment comprising libraries for implementing an image processing algorithm and an object detection algorithm.

11. The method of claim 7 further configured to integrate said chest X-ray image with a clinical data, including at least a laboratory data and a patient history, thus improving a diagnostic precision and a reliability.

12. A method for detecting pneumonia in a chest X-ray image comprising:

acquiring a dataset of medical images comprising at least three pneumonia-infected lung images and at least three healthy lung images;

pre-processing said dataset of medical images to standardize and partition said dataset of medical images into a training subset, a validation subset, and a testing subset;

training one or more convolutional neural networks (CNN) for an image processing and an object detection using said training subset;
tuning said training to optimize performance for a pneumonia detection;
evaluating said training using said validation subset and computing a set of performance metrics;
executing computations and simulations on a cloud-based platform; and
detecting a pneumonia in said chest X-ray image based on said training subset and said validation subset;
computing an accuracy determined from the percentage of a set of pneumonia predictions correct;
computing a precision determined from said set of pneumonia predictions by calculating the ratio of true positive pneumonia predictions to all positive pneumonia predictions;
computing a recall determined from an ability of said method to detect all actual pneumonia cases by computing the ratio of true positive pneumonia predictions to the total real pneumonia cases; and
computing an F1-score determined from said precision and said recall;
wherein said method is configured to provide early and accurate pneumonia screening, thus enabling life-saving treatment.

* * * * *